(12) United States Patent
Bharucha et al.

(10) Patent No.: US 10,194,813 B2
(45) Date of Patent: Feb. 5, 2019

(54) SYSTEMS, DEVICES AND METHODS FOR ASSESSMENT OF BODY CAVITY PRESSURES

(71) Applicant: Mayo Foundation for Medical Education and Research, Rochester, MN (US)

(72) Inventors: Adil E. Bharucha, Rochester, MN (US); Randolph W. Stroetz, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/483,578

(22) Filed: Apr. 10, 2017

(65) Prior Publication Data

US 2017/0209057 A1    Jul. 27, 2017

Related U.S. Application Data

(62) Division of application No. 13/386,211, filed as application No. PCT/US2010/043474 on Jul. 28, 2010.

(Continued)

(51) Int. Cl.
*A61B 5/03* (2006.01)
*A61B 5/00* (2006.01)

(52) U.S. Cl.
CPC ............... *A61B 5/036* (2013.01); *A61B 5/42* (2013.01); *A61B 5/4255* (2013.01); *A61B 5/6853* (2013.01); *A61B 2562/0247* (2013.01)

(58) Field of Classification Search
CPC ..... A61B 5/036; A61B 5/4255; A61B 5/6853; A61B 2562/0247
See application file for complete search history.

(56) References Cited

U.S. PATENT DOCUMENTS 4,600,015 A * 7/1986 Evans .................... A61B 5/037
600/593
5,533,969 A    7/1996 Mulder
(Continued)

FOREIGN PATENT DOCUMENTS

EP    1654977 A1    5/2006
EP    1731084 A1    12/2006
(Continued)

OTHER PUBLICATIONS

International Preliminary Report on Patentability, dated Feb. 9, 2012, Patent Application No. PCT/US2010/043474.
(Continued)

*Primary Examiner* — Jeffrey G Hoekstra
*Assistant Examiner* — Jonathan M Foreman
(74) *Attorney, Agent, or Firm* — Mueting, Raasch & Gebhardt, P.A.

(57) ABSTRACT

Systems, devices and methods that can be used to obtain objective pressure measurements in a body cavity using one or more monitoring bladders mounted on a catheter. The monitoring bladders may be adapted to connect or be connected to a system capable of providing objective pressure measurements indicative of the compressive forces acting on the one or more monitoring bladder in the body cavity. The body cavity may include, for example, the rectum, esophagus, stomach, intestine, colon, reproductive tract, urethra, oronasopharnygeal tract, etc.

7 Claims, 4 Drawing Sheets

Related U.S. Application Data (60) Provisional application No. 61/229,529, filed on Jul. 29, 2009.

(56) References Cited

U.S. PATENT DOCUMENTS

| | | | |
|---|---|---|---|
| 5,653,240 | A | 8/1997 | Zimmon |
| 5,919,163 | A | 7/1999 | Glickman |
| 6,773,452 | B2 | 8/2004 | Shaker |
| 2001/0053920 | A1 | 12/2001 | Shaker |
| 2002/0115982 | A1 | 8/2002 | Barbut |
| 2004/0171942 | A1 | 9/2004 | Ackerman et al. |
| 2005/0261582 | A1 | 11/2005 | Becker et al. |
| 2006/0212022 | A1 | 9/2006 | Gellman |
| 2008/0027505 | A1 | 1/2008 | Levin et al. |
| 2009/0203995 | A1* | 8/2009 | Matonick .......... A61M 25/1011 600/435 |
| 2009/0275924 | A1 | 11/2009 | Lattanzio et al. |
| 2011/0295236 | A1 | 12/2011 | Gregory |
| 2012/0179063 | A1 | 7/2012 | Bharucha et al. |

FOREIGN PATENT DOCUMENTS

| | | |
|---|---|---|
| EP | 1892010 A1 | 2/2008 |
| FR | 2652495 A1 | 4/1991 |
| JP | 2002-503513 | 2/2002 |
| JP | 2003-527918 | 9/2003 |
| JP | 2005-296258 | 10/2005 |
| JP | 2006-130207 | 5/2006 |
| WO | WO 97/03604 A1 | 2/1997 |
| WO | WO 99/42045 A1 | 8/1999 |
| WO | WO 01/72221 A1 | 10/2001 |
| WO | WO 02/068036 A1 | 9/2002 |

OTHER PUBLICATIONS

International Search Report and Written Opinion, dated Mar. 24, 2011, Patent Application No. PCT/US2010/043474.

Supplementary European Search Report, dated Oct. 29, 2013, EP Application No. 10804970.1, and claims 1-15 on which the report was issued.

* cited by examiner

SYSTEMS, DEVICES AND METHODS FOR ASSESSMENT OF BODY CAVITY PRESSURES

The present application is a divisional application of U.S. patent application Ser. No. 13/386,211, titled SYSTEMS, DEVICES AND METHODS FOR ASSESSMENT OF BODY CAVITY PRESSURES which is a U.S. National Stage Application of International Application No. PCT/US2010/043474, titled SYSTEMS, DEVICES AND METHODS FOR ASSESSMENT OF BODY CAVITY PRESSURES, filed on Jul. 28, 2010, published in the English language on Feb. 3, 2011 as International Publication No. WO 2011/014530 A2, which claims the benefit under 35 U.S.C. § 119(e) of U.S. Provisional Patent Application No. 61/229,529, filed on Jul. 29, 2009 and titled SYSTEMS, DEVICES AND METHODS FOR ASSESSMENT OF BODY CAVITY PRESSURES, all of which are hereby incorporated by reference in their entirety.

Systems, devices and methods for objective assessment of body cavity pressures such as, e.g., anorectal pressures) are described herein.

Among body cavities, the anal canal is responsible for maintaining continence, i.e., preventing stool from leaking under normal circumstances. The rectum is a reservoir that holds stool until defecation is convenient. The anal canal is surrounded by sphincters made of muscles that are responsible for keeping the canal closed at rest. Normal defecation requires increased rectal pressures coordinated with anal relaxation. The sphincters can also contract further to maintain continence when defecation is inconvenient. In some patients, however, anal pressures may be reduced due to disease, injury, etc. In other patients, anal pressures may be increased such that they cause constipation. In addition, anal pressures normally decline with age and are lower in women than in men.

Anal pressures may be subjectively assessed by practitioners using a finger or digit inserted into the anal canal of the patient. The subjective nature of such assessments may, however, lead to inconsistent diagnoses, particularly with less-experienced practitioners.

Systems for the objective measurement of anorectal pressures have been developed. Anal pressures are measured in such systems using solid-state or water-perfused sensors attached to a catheter inserted in the anal canal. The testing generally requires cumbersome equipment, is typically conducted by trained technicians in specialized laboratories, and requires 30 to 45 minutes to complete and can be costly, e.g., $350 to $1000. Those factors effectively preclude the use of the tests in many settings.

SUMMARY

Systems, devices and methods are described herein that can be used to obtain objective pressure measurements in a body cavity using one or more monitoring bladders mounted on a catheter. The monitoring bladders may preferably be adapted to connect or be connected to a system capable of providing objective pressure measurements indicative of the compressive forces acting on the one or more monitoring bladder in the body cavity.

In some embodiments, the pressure measuring device may include an optional distention device that can potentially hold the pressure measuring device in a stationary location within the body cavity. If used to measure rectal pressures, the distention device may be used to elicit the urge to defecate.

The body cavity pressure measurement systems described herein include, in some embodiments, a pressure measuring device that includes a catheter having a proximal end and a distal end; a distention device mounted on the catheter proximate the distal end of the catheter, wherein the distention device is expandable and collapsible between a collapsed configuration and a distended configuration; a monitoring bladder mounted on the catheter at a location proximal to the distention device, wherein the monitoring bladder is movable along the catheter between a first position proximate the distention device and a second position located proximal of the first position; and a monitoring lumen extending proximally through at least a portion of the catheter from the monitoring bladder towards the proximal end of the catheter, wherein the monitoring lumen is in fluid communication with an interior of the monitoring bladder such that a fluid pressure in the monitoring bladder is communicated through the monitoring lumen. The body cavity pressure measurement systems also include a pressure monitoring apparatus operably connected to the monitoring bladder of the pressure measuring device through the monitoring lumen, wherein the pressure monitoring apparatus is configured to determine the fluid pressure in the monitoring bladder by measuring fluid pressure in the monitoring lumen at a proximal end of the monitoring lumen.

In some embodiments, the distention device is mounted at a fixed position on the catheter.

In some embodiments, the distention device, in the distended configuration, has a maximum transverse dimension that is larger than a maximum transverse dimension of the pressure measuring device in the length occupied by the monitoring bladder, wherein the maximum transverse dimensions are measured transverse to the longitudinal axis.

In some embodiments, the distention device has an inflatable chamber that is inflated to expand the distention device to the distended configuration and wherein the inflatable chamber is deflated to collapse the distention device to the collapsed configuration. The distention device may also include a distention lumen extending proximally through at least a portion of the catheter from the distention device towards the proximal end of the catheter, wherein the distention lumen is in fluid communication with the inflatable chamber.

In some embodiments, the catheter includes a movable sleeve positioned proximal of the distention device, wherein the monitoring bladder is mounted on the movable sleeve, and wherein the movable sleeve moves along the catheter when the monitoring bladder moves along the catheter between the first position proximate the distention device and the second position located proximal of the first position of the catheter.

In some embodiments, the systems include an inflation lumen extending proximally through at least a portion of the catheter from the monitoring bladder towards the proximal end of the catheter, wherein the inflation lumen is in fluid communication with the interior of the monitoring bladder fluid can be delivered to the monitoring bladder through the inflation lumen. In some embodiments, the inflation lumen and the monitoring lumen are different lumens.

In some embodiments, the monitoring lumen has a proximal end connected to the pressure monitoring apparatus through a detachable coupling.

In some embodiments, the pressure measuring device includes two or more monitoring bladders and two or more monitoring lumens; wherein each monitoring bladder of the two or more monitoring bladders is mounted on the catheter at a location proximal to the distention device, wherein each monitoring bladder is movable along the catheter between a first position proximate the distention device and a second position located proximal of the first position; and wherein each monitoring lumen of the two or more monitoring lumens extends proximally through at least a portion of the catheter from the monitoring bladder towards the proximal end of the catheter, wherein each monitoring lumen is in fluid communication with an interior of one monitoring bladder such that a fluid pressure in the one monitoring bladder is communicated through the monitoring lumen. In some embodiments, the two or more monitoring bladders are positioned about a periphery of the catheter at the same longitudinal position, wherein each monitoring bladder occupies only a portion of the periphery of the catheter.

In some embodiments, the system further includes a medical electrode mounted on the catheter proximate the monitoring bladder; an electrical lead operably connected to the medical electrode and extending proximally through at least a portion of the catheter; and electrical monitoring apparatus operably connected to the medical electrode through the electrical lead, wherein the electrical monitoring apparatus is configured to detect electrical activity in tissue contacting the medical lead. In some embodiments, the medical lead is attached to an expandable support that is expandable and collapsible between a collapsed configuration and an expanded configuration, wherein the medical electrode is closer to the catheter when the expandable support is in the collapsed configuration than when the expandable support is in the expanded configuration. In some embodiments, the expandable support includes shape memory material, an expandable balloon, etc.

The body cavity pressure measuring devices described herein include, in some embodiments, a catheter having a proximal end and a distal end; a distention device mounted on the catheter proximate the distal end of the catheter; wherein the distention device is expandable and collapsible between a collapsed configuration and a distended configuration; a monitoring bladder mounted on the catheter at a location proximal to the distention device, wherein the monitoring bladder is movable along the catheter between a first position proximate the distention device and a second position located proximal of the first position; and a monitoring lumen extending proximally through at least a portion of the catheter from the monitoring bladder towards the proximal end of the catheter, wherein the monitoring lumen is in fluid communication with an interior of the monitoring bladder such that a fluid pressure in the monitoring bladder is communicated through the monitoring lumen.

In some embodiments of the body cavity pressure measuring devices described herein, the distention device is mounted at a fixed position on the catheter.

In some embodiments of the body cavity pressure measuring devices described herein, the distention device, in the distended configuration, has a maximum transverse dimension that is larger than a maximum transverse dimension of the pressure measuring device in the length occupied by the monitoring bladder, wherein the maximum transverse dimensions are measured transverse to the longitudinal axis.

In some embodiments of the body cavity pressure measuring devices described herein, the distention device has an inflatable chamber that is inflated to expand the distention device to the distended configuration and wherein the inflatable chamber is deflated to collapse the distention device to the collapsed configuration. In some embodiments, the device includes a distention lumen extending proximally through at least a portion of the catheter from the distention device towards the proximal end of the catheter, wherein the distention lumen is in fluid communication with the inflatable chamber.

In some embodiments of the body cavity pressure measuring devices described herein, the catheter includes a movable sleeve positioned proximal of the distention device, wherein the monitoring bladder is mounted on the movable sleeve, and wherein the movable sleeve moves along the catheter when the monitoring bladder moves along the catheter between the first position proximate the distention device and the second position located proximal of the first position of the catheter.

In some embodiments of the body cavity pressure measuring devices described herein, the device includes an inflation lumen extending proximally through at least a portion of the catheter from the monitoring bladder towards the proximal end of the catheter, wherein the inflation lumen is in fluid communication with the interior of the monitoring bladder fluid can be delivered to the monitoring bladder through the inflation lumen. In some embodiments, the inflation lumen and the monitoring lumen are different lumens.

In some embodiments of the body cavity pressure measuring devices described herein, the monitoring lumen has a proximal end comprising a detachable coupling.

In some embodiments of the body cavity pressure measuring devices described herein, the device includes two or more monitoring bladders and two or more monitoring lumens; wherein each monitoring bladder of the two or more monitoring bladders is mounted on the catheter at a location proximal to the distention device, wherein each monitoring bladder is movable along the catheter between a first position proximate the distention device and a second position located proximal of the first position; and wherein each monitoring lumen of the two or more monitoring lumens extends proximally through at least a portion of the catheter from the monitoring bladder towards the proximal end of the catheter, wherein each monitoring lumen is in fluid communication with an interior of one monitoring bladder such that a fluid pressure in the one monitoring bladder is communicated through the monitoring lumen. In some embodiments, the two or more monitoring bladders are positioned about a periphery of the catheter at the same longitudinal position, wherein each monitoring bladder occupies only a portion of the periphery of the catheter.

In some embodiments of the body cavity pressure measuring devices described herein, the device includes a medical electrode mounted on the catheter proximate the monitoring bladder; and an electrical lead operably connected to the medical electrode and extending proximally through at least a portion of the catheter. In some embodiments, the medical lead is attached to an expandable support that is expandable and collapsible between a collapsed configuration and an expanded configuration, wherein the medical electrode is closer to the catheter when the expandable support is in the collapsed configuration than when the expandable support is in the expanded configuration. In some embodiments, the expandable support includes shape memory material, an expandable balloon, etc.

Methods of monitoring internal body cavity pressures described herein include, in some embodiments, using the body cavity pressure measuring devices and/or the pressure monitoring apparatus that are also described herein. The methods may, in some embodiments, include locating a pressure measuring device described herein in a body cavity; expanding the distention device on the pressure measuring device; monitoring pressure exerted on the monitoring bladder by the body cavity; and moving the monitoring bladder relative to the distention device to monitor pressure exerted on the monitoring bladder at two or more locations relative to the body cavity while holding the distention device stationery relative to the body cavity.

Some embodiments of the systems and devices described herein may potentially be used to facilitate pelvic floor retraining by biofeedback therapy. Biofeedback therapy is used to improve pelvic floor motion in patients with, among other conditions, defecatory disorders and fecal incontinence. The systems and devices described herein may, by virtue of their lower cost and simplicity, facilitate the application of manometry for providing pelvic floor retraining in locations outside of laboratories such as, e.g., clinics, long-term care facilities, operating rooms, homes, etc.

These and other features and advantages of the present invention may be described below in connection with one or more exemplary embodiments of the invention.

DESCRIPTION OF ILLUSTRATIVE EMBODIMENTS

In the following detailed description of some illustrative embodiments of the body cavity pressure measurement systems described herein, reference is made to the accompanying figures of the drawing which form a part hereof, and in which are shown, by way of illustration, specific embodiments in which the body cavity pressure measurement systems described herein may be practiced. Elements from one embodiment may be used in combination with elements of the other embodiments, i.e., the number of potential embodiments using combinations of features set forth herein is not limited to the specific embodiments shown in the figures and/or described herein. Further, the embodiments described herein may include elements that are not shown to scale.

Figures 1, 2:
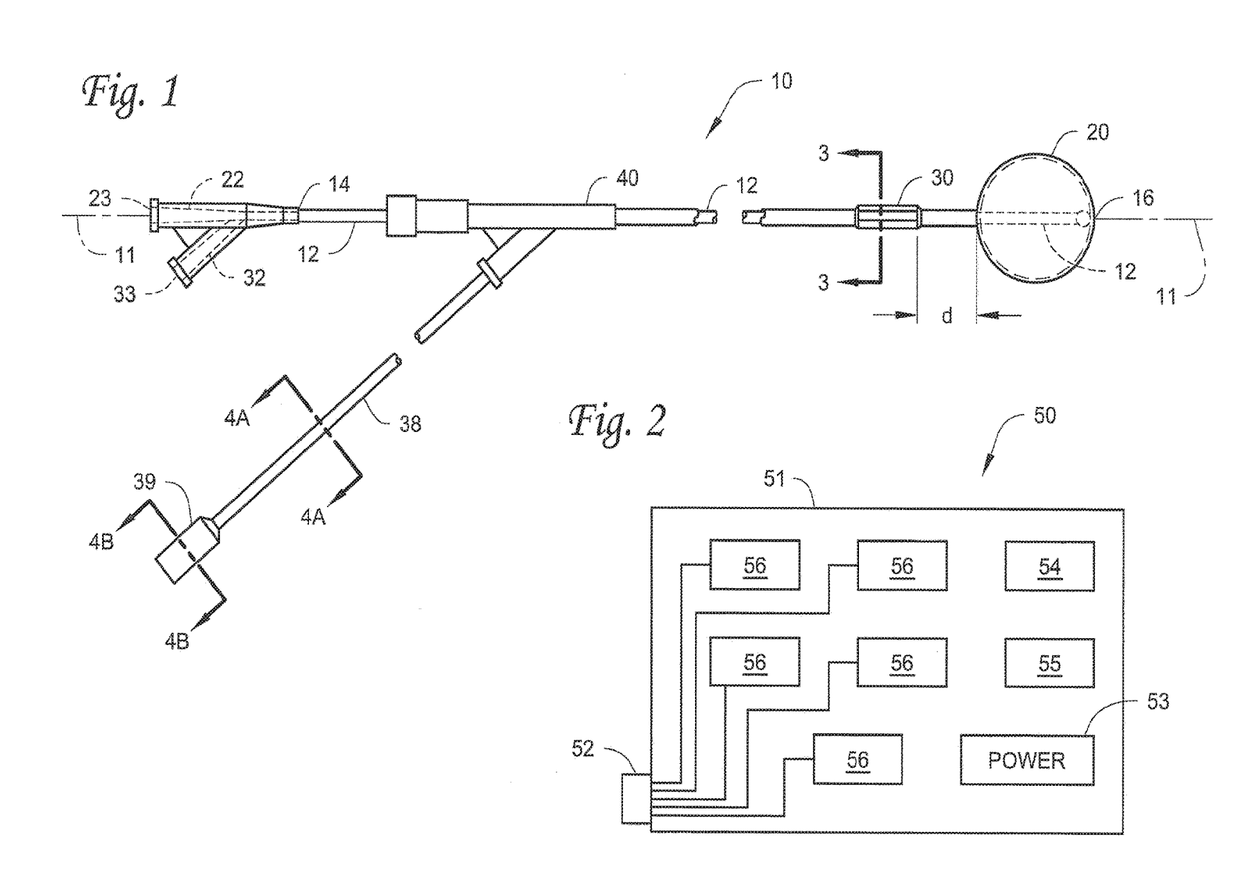
FIG. 1 is a view of one embodiment of pressure measuring device that may be used in the body cavity pressure measurement systems described herein.
FIG. 2 is a block diagram of one embodiment of a pressure monitoring apparatus that may be used in the body cavity pressure measurement systems described herein.

One illustrative embodiment of a pressure measurement device according to the present invention is depicted in FIG. 1. The device 10 depicted in FIG. 1 is in the form of an elongated device designed for placement in an internal body cavity in which pressure measurements are to be taken. The device 10 may be placed in the body cavity through a natural orifice (e.g. anus, vagina, esophagus, etc.) or it may be placed through an access site created for the purpose of placing the device 10 (e.g., an incision, etc.).

For the purposes of simplicity, the elongated body portion 12 of the device 10 will be described as a catheter, although such a description should not be used to limit device 10 to anything other than an elongated body having a proximal end 14 and a distal end 16 defining a longitudinal axis 11 that extends through the proximal end 14 and the distal end 16. The device 10 is adapted for placement in an internal body cavity such as the rectum, esophagus, stomach, intestine, colon, reproductive tract, urethra, oronasopharnygeal tract, etc. As a result, the device 10 may be provided in a variety of different sizes to accommodate a variety of different body cavity sizes and shapes.

Among the various components that may be included in the device 10 is a distention device 20. The distention device 20 may preferably be mounted on the catheter 12 proximate the distal end 16 of the catheter 12. Although the distention device 20 is depicted as being located at the distal end 16, the distention device 20 may, in some embodiments be located at a position that is proximal of the most distal portion of the catheter 12.

The distention device 20 is preferably expandable and collapsible between a collapsed configuration and a distended configuration. As depicted in FIG. 1, the distention device 20 is in the distended configuration. When in the distended configuration, the distention device is larger than when the distention device 20 is in the collapsed configuration. When in the collapsed configuration, the distention device has a smaller profile that is closer to the size of the catheter 12 on which the distention device 20 is located. The collapsed configuration of the distention device 20 may be useful to ease insertion and/or removal of the device 10 from a body cavity. The distention device 20 may be mounted on the catheter 12 at a fixed position such that the distention device 20 cannot move along the length of the catheter 12 (where the length of the catheter 12 is determined along a longitudinal axis extending through the proximal end 14 and distal end 16 of the catheter).

The distention device 20 may be expandable through any suitable technique or combination of techniques. In some embodiments, the distention device 20 may be expanded into the distended configuration through inflation of an inflatable chamber located in the distention device 20. In such an embodiment, the distention device 20 may be collapsed by deflating the inflatable chamber. To facilitate the collapse and distention, the distention device 20 may preferably be constructed using flexible fluid impermeable materials such as, e.g., polymer films, impermeable fabrics, etc.

Inflation of the inflatable chamber in the distention device 20 may be accomplished by delivering one or more fluids (e.g., liquids, gases, slurries, suspensions, gels, etc.) to the inflatable chamber in the distention device 20. The fluids may be delivered to the inflatable chamber of the distention device 20 though a distention lumen 22 that extends proximally through at least a portion of the catheter 12 from the distention device 20 towards the proximal end 14 of the catheter 12. The distention lumen 22 is in fluid communication with the inflatable chamber of the distention device 20 such that fluids passing through the distention lumen 22 can enter the inflatable chamber of the distention device 20. The distention lumen 22 preferably includes a port 23 through which the fluids to be delivered to the inflatable chamber of the distention device are introduced. The fluids may be delivered to the port 23 using a syringe or any other acceptable fluid supply device (e.g., pump, pressurized reservoir, etc.).

Although the distention device 20 in the depicted embodiment uses an inflatable chamber to move between collapsed and distended configurations, in other embodiments the distention device may move between the collapsed and distended configurations using other expandable structures. Potentially suitable examples of alternative collapsible/expandable structures may include, e.g., structures constructed of shape memory materials, metals, polymers, miniature deformation engineerable structures, etc.

The embodiment of the pressure measurement device 10 depicted in FIG. 1 also includes one or more monitoring bladders 30 that, in the depicted embodiment, are located proximally from the distention device 20 such that the distention device 20 is located between the distal end 16 of the catheter 12 and the one or more monitoring bladders 30. The monitoring bladders 30 are also seen in the cross-sectional view of FIG. 3 (taken along line 3-3 in FIG. 1).

The monitoring bladders 30 are provided to detect compressive pressure exerted on the device 10 by the walls of the body cavity in contact with the monitoring bladders 30. The bladders 30 may preferably be constructed of flexible, fluid-impermeable materials such as, e.g., polymer films, fabrics, etc. In the depicted embodiment, the monitoring bladders 30 may contain one or more fluids (e.g., liquids, gases, slurries, suspensions, gels, etc.). The amount of fluid contained in the monitoring bladders 30 may, in some embodiments such as that depicted in FIG. 1 be adjustable. The embodiment of device 10 includes an inflation lumen 32 in fluid communication with the one or more monitoring bladders 30 to adjust the amount of fluid contained in the bladders 30. The inflation lumen 32 in the depicted embodiment includes an inflation port 33 proximate the proximal end 14 of the catheter 12. The inflation fluids may be delivered to the port 33 using a syringe or any other acceptable fluid supply device (e.g., pump, pressurized reservoir, etc.).

In other embodiments, the amount of fluid contained in the one or more monitoring bladders 30 may be fixed. In still other embodiments that include a plurality of bladders 30, the amount of fluid contained in one or more of the bladders 30 may be fixed and the amount of fluid contained in one or more other bladders may be adjustable using, e.g., an inflation lumen 32. Reducing the amount of fluid in the monitoring bladders 30 may be used to reduce the profile or size of the device 10 to facilitate placement and/or removal of the device 10, while increasing the amount of fluid in the monitoring bladders 30 may facilitate measurement of body cavity pressures.

In some embodiments, the distention device 20 maybe characterized as having, in its distended configuration, a maximum transverse dimension that is larger than a maximum transverse dimension of the pressure measuring device in the length occupied by the monitoring bladder(s) 30 (where the maximum transverse dimension is also measured transverse to the longitudinal axis 11). As used herein, the "maximum transverse dimension" is the largest dimension of the component (e.g., distention device 20, etc.) as measured in a cross-sectional plane that is transverse to the longitudinal axis 11. As an example, where the distention device 20 is in the form of a device having a circular cross-section in a plane that is transverse to the longitudinal axis 11, the maximum transverse dimension is the diameter of that circular cross-section. The cross-sectional plane in which the maximum transverse dimension of the distention device 20 is determined may intersect the longitudinal axis 11 at any location along the portion of the longitudinal axis that is occupied by the distention device 20. With respect to the maximum transverse dimension of the pressure measuring device in the length occupied by the monitoring bladder or bladders 30, the cross-sectional plane in which the maximum transverse dimension is determined may intersect the longitudinal axis 11 at any location along the portion of the longitudinal axis that is occupied by the bladder or bladders 30 (although the maximum transverse dimension may often be found proximate the midpoint of the length of the bladder or bladders 30).

Where more than one monitoring bladder 30 is provided, the inflation lumen 32 may, in some embodiments, inflate/deflate all of the monitoring bladders 30 equally while in other embodiments, the monitoring bladders 30 may potentially selectively inflate/deflate selected monitoring bladders 30.

In the depicted embodiment, the device includes five monitoring bladders arranged about the periphery of the catheter 12 such that each of the bladders 30 can monitor pressure over an arcuate portion of the periphery of the catheter 12. Other embodiments may include as few as one monitoring bladder or any other suitable number of bladders (e.g., two, three, four, six, etc.). It may be preferred that the bladders 30 are positioned at the same location along the length of the catheter 12 (as seen in FIG. 1), although in other embodiments monitoring bladders may be longitudinally displaced from each other along the length of the catheter 12.

The pressure measuring device 10 also includes one or more monitoring lumens 36 that extend proximally through at least a portion of the catheter 12 from the one or more monitoring bladders 30 towards the proximal end 14 of the catheter 12. Each of the one or more monitoring lumens 36 are in fluid communication with an interior of one of the monitoring bladders 30 such that a fluid pressure in the monitoring bladder 30 is communicated back towards the proximal end of the device 10 through the monitoring lumen 36.

Figure 4A:
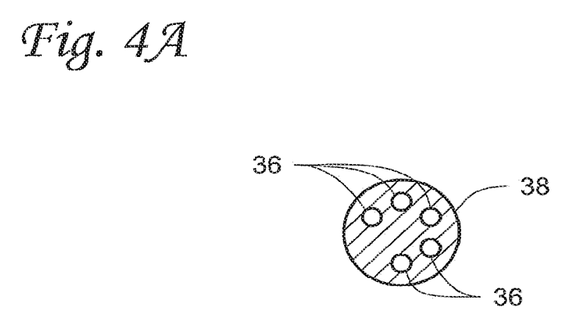
FIG. 4A is a cross-sectional view of the pressure measuring device of FIG. 1 taken along line 4A-4A in FIG. 1.
Figure 4B:
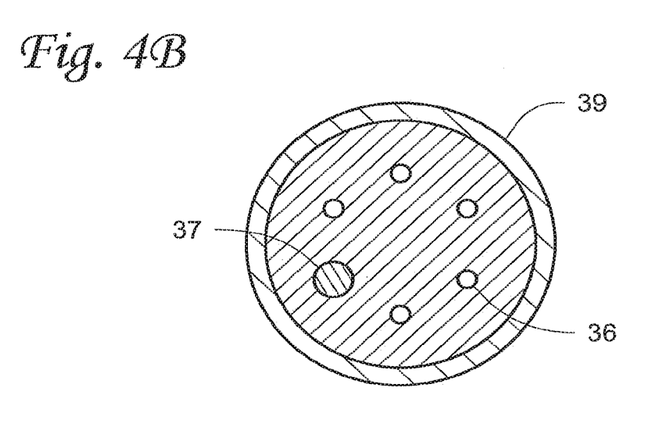
FIG. 4B is a cross-sectional view of the pressure measuring device of taken along line 4B-4B in FIG. 1.

As seen in the combination of FIGS. 1, 4A and 4B with respect to the depicted embodiment, the monitoring lumens 36 terminate in a coupling 39 that is located at the end of a branch 38 that extends off of the catheter 12. The monitoring lumens 36 extend through the branch 38 to the coupling 39 where they can be connected to a pressure monitoring apparatus 50 (one embodiment of which is depicted in FIG. 2). A cross-sectional view of the branch 38 is depicted in FIG. 4A to show the different monitoring lumens 36 extending therethrough. The cross-sectional view of the coupling 39 depicted in FIG. 4B shows that the coupling 39 may include an alignment mechanism such as, e.g., a pin 37 such that the monitoring lumens 36 in the coupling 39 can be selectively coupled to the pressure monitoring apparatus 50.

Figure 3:
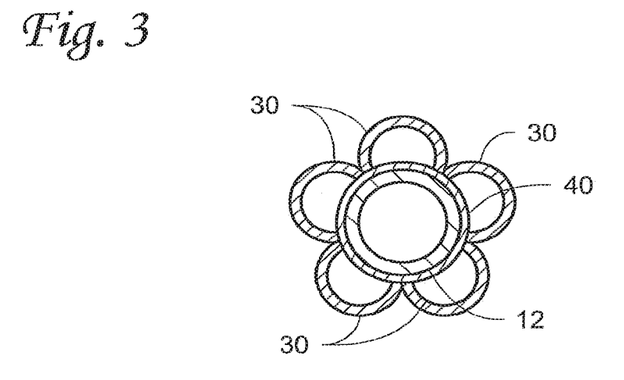
FIG. 3 is a cross-sectional view of the pressure measuring device of FIG. 1 taken along line 3-3 in FIG. 1.

Yet another feature depicted in connection with the embodiment of FIGS. 1 and 3 is that the catheter 12 may include a movable sleeve 40 such that the distention device 20 and the monitoring bladders 30 can be moved relative to each other. Movement of the sleeve 40 can be used to adjust the distance d (see, e.g., FIG. 1) between the distention device 20 and the one or more monitoring bladders 30.

Such movement can be used to allow for adjustment of the position of the bladders 30 if the region of the body cavity from which pressure measurements are needed can vary. Movement of the sleeve 40 and attached monitoring bladders 30 can also be used to obtain measurements along a length of the body cavity while the distention device 20 and the catheter 12 to which it is attached remain stationary within the body cavity.

The sleeve 40 may be continuous both along the catheter and around the catheter, although a myriad of alternate constructions are possible so long as the monitoring bladders 30 and the distention device 20 can be moved longitudinally relative to each other.

In some embodiments, rotational position of the sleeve 40 relative to the catheter 12 and/or distention device 20 may be fixed or adjustable. Adjustment of the sleeve 40 and the bladders 30 may be accomplished by rotating the sleeve 40 about the catheter 12.

Although not depicted in FIG. 1, the distention device 20 may, in some embodiments, include or be operably connected to a pressure measurement device such that the pressure exerted on the distention device 20 by the body cavity can be measured during use of the device 10.

Referring to FIG. 2, one embodiment of a pressure monitoring apparatus 50 that can be used in conjunction with the pressure measurement device 10 is depicted in block diagram format. The apparatus 50 as depicted in FIG. 2 includes a housing 51 and a coupling 52 that is adapted to connect to the coupling 39 of the pressure measuring device 10. Pressure sensors 56 are operatively connected to the coupling 52 such that the pressure within the monitoring lumens 36 and, thus, the monitoring bladders 30 can be measured. Although the depicted embodiment includes a separate, dedicated pressure sensor 56 corresponding to each of the monitoring bladders 30, in some embodiments more than one monitoring bladder 30 may be connected to the same pressure sensor through a switching assembly so that the pressure within the different monitoring bladders 30 can be obtained by selectively connecting the pressure sensor to the different monitoring bladders.

The connections between the pressure sensors 56 in the pressure monitoring apparatus 50 and the monitoring bladders 30 on the pressure measuring device 10 may preferably be limited to fluid connections (e.g., a pneumatic connection, etc.). The couplings 39 and 52, in such an embodiment, preferably form fluid-tight connections between the monitoring lumens 36 and the coupling 52 on the apparatus 50. A potential benefit of a pneumatic connection may be that the device 10 itself need not carry any electronic components, etc.

As discussed herein, in some embodiments, the pressure monitoring apparatus 50 may also be operably connected to the distention device 20 to measure pressures on or in the distention device 20 in addition to the monitoring bladder(s) 30. As with bladders 30, the apparatus 50 may include a dedicated pressure sensor for the distention device 20 or a pressure senor in the apparatus 50 may be selectively coupled to the distention device 20 to monitor pressure on or in the distention device 20.

Apparatus 50 also includes an optional power supply 53, along with a controller 54 and memory/data transfer component 55. The power supply 53 may be self-contained on the apparatus 50 (e.g., a battery, fuel cell, capacitive power supply, etc.) or power may be supplied externally of the apparatus 50. The controller 54 may be embodied in any suitable combination of hardware and/or software that is capable of providing the functions described herein. The memory/data transfer component 55 may be provided in the form of on-board data storage medium and/or data transfer equipment (e.g., cables, telemetry devices such as RF transceivers, Bluetooth, infrared communication equipment, etc.).

Memory associated with the apparatus 50 may be, e.g., any computer readable medium that stores processor executable software instructions that can be applied by the processor. By way of example, suitable memory may be random access memory (RAM), read-only memory (ROM), non-volatile random access memory (NVRAM), electrically erasable programmable read-only memory (EEPROM), flash memory, etc.

The data collected using the pressure sensors 56 may be stored on-board the apparatus 50 for processing by the controller 54, downloaded or transferred to other processing equipment (e.g., a personal computer, etc.), and/or transmitted during acquisition to another processing device. Real-time on-board data processing and/or data transfer to another data processing device (e.g., a personal computer, etc.) for real-time data processing may allow a practitioner to obtain additional data where the collected data is either flawed or indicative of the need for further data collection (e.g., indicative of a condition that may require the collection of additional data for accurate assessment of the condition).

Figure 5:
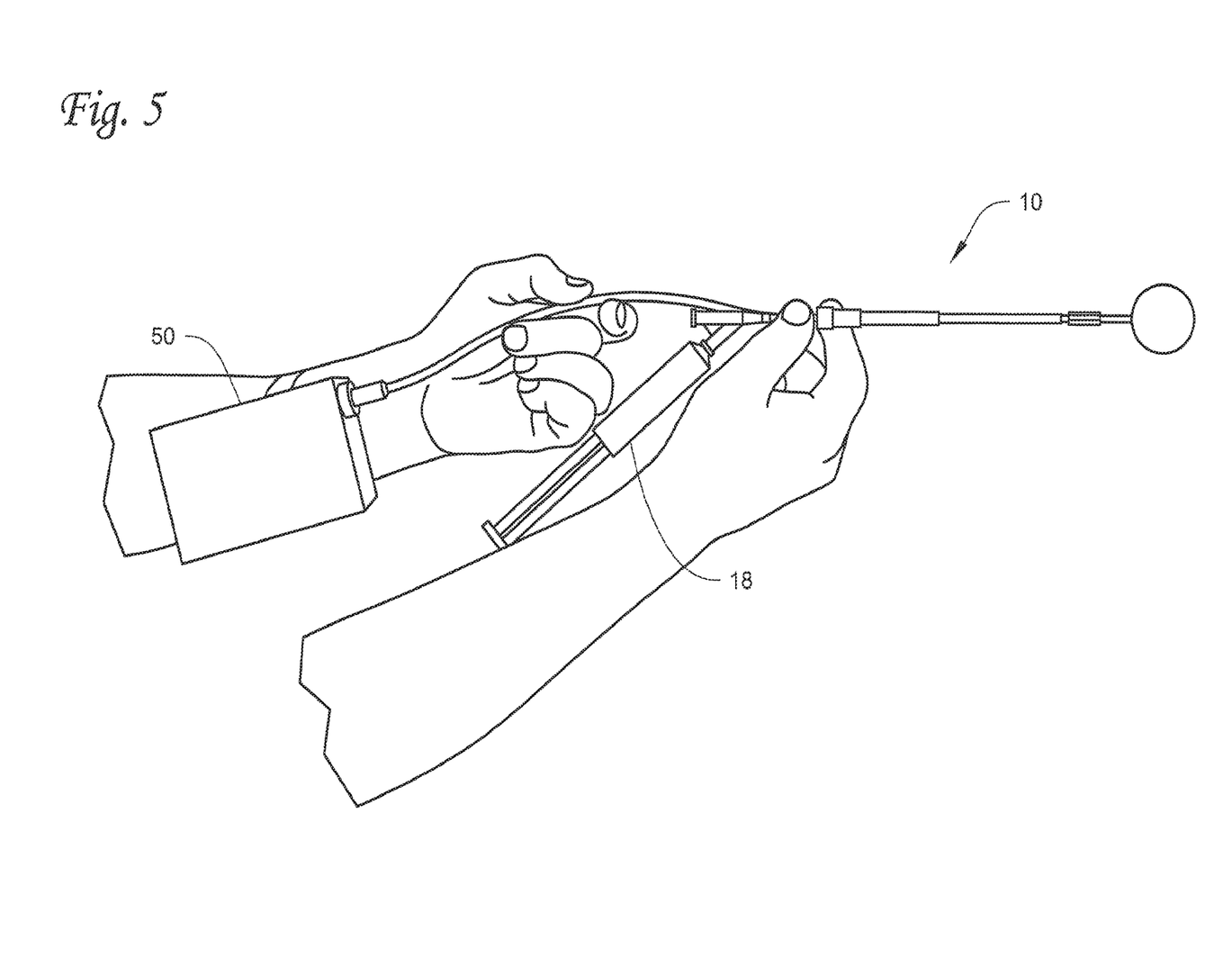
FIG. 5 depicts use of one embodiment of a body cavity pressure measurement system as described herein.

The pressure monitoring apparatus 50 may preferably be provided in a portable housing 51 that may, for example, be attached to the forearm or another location on the user. FIG. 5 depicts the pressure monitoring apparatus 50 attached to the left forearm of a user, while the right hand of the user is used to manipulate the pressure monitoring device 10 attached to the apparatus 50. By attaching the apparatus 50 the user, flexibility of use and ease of use may potentially be enhanced. If, for example, the pressure monitoring apparatus is attached to the non-dominant forearm/wrist of a user, the user's dominant hand may be free to manipulate the pressure measurement device and/or operate other devices such as, for example, the pressure monitoring apparatus 50 itself, a computer to which the collected data is transmitted from the apparatus 50, etc. The dominant hand may also be used to operate a syringe 18 attached to a port on the pressure measurement device 10.

Figure 6:
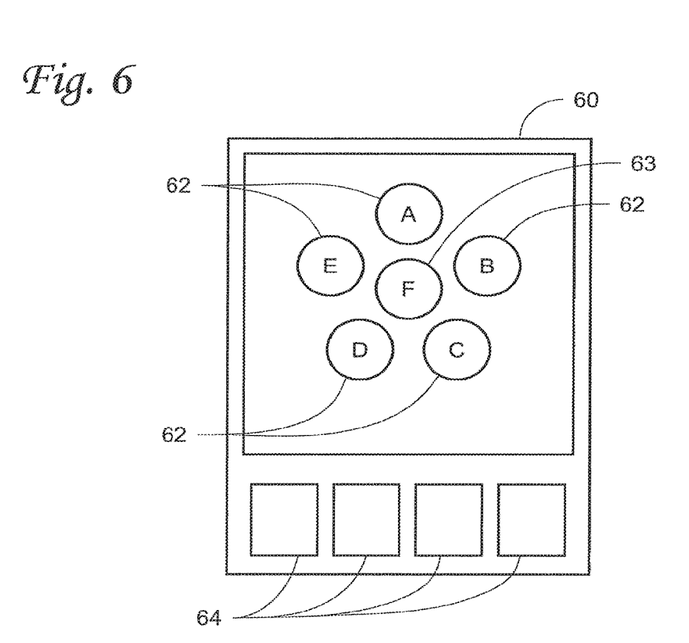
FIG. 6 is a block diagram of one embodiment of a display providing pressure data to a user of the body cavity pressure measurement systems described herein.

The data collected using the pressure monitoring apparatus 50 and an associated pressure measuring device 10 may be output in any suitable format. One embodiment of a potentially useful format is depicted in FIG. 6 in which a display device (e.g., computer monitor, etc.) 60 includes pressure outputs 62 (also denoted as outputs A, B. C, D, and E) arranged in the same spatial relationship about a central output 63 (also denoted as output F) as the monitoring bladders 30 used to obtain the data are arranged around the catheter 12. Such data outputs may be helpful to locate the portion of tissue in a body cavity that may be diseased or otherwise not functioning properly.

In some embodiments, the central output 63 may be sued to provide an average of all of the bladder-specific outputs 62 or other information (e.g., the distention device pressure, location along a reference axis, etc.).

Other outputs 64 may be provided to supply a user with information such as pressure plots depicting pressure variations in the bladders over time, pressure in the distention device, etc.

Figure 7:
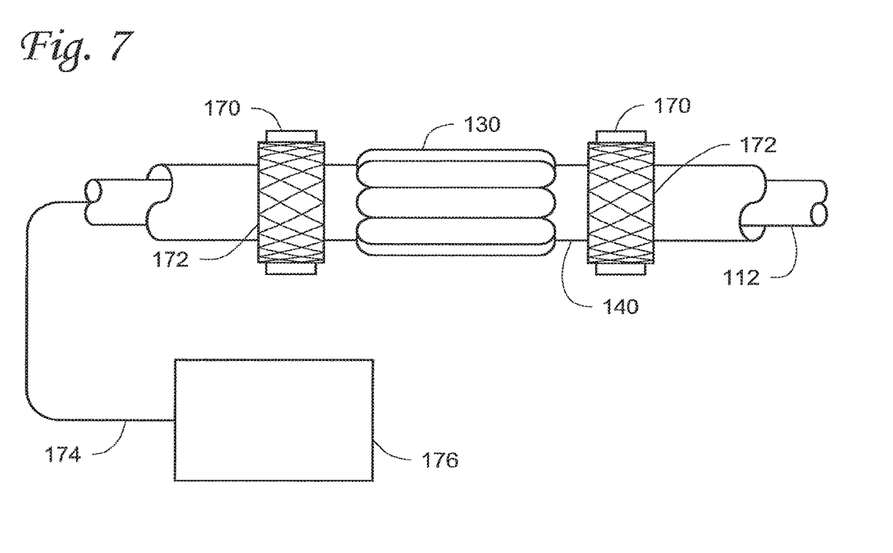
FIG. 7 is a diagram of a pressure measurement device including electrodes and an electrical monitoring apparatus connected to the electrodes.

Still another optional feature of the body cavity pressure measurement systems described herein is depicted in FIG. 7. The view in FIG. 7 is of a portion of another embodiment of a pressure measurement device that includes a portion of a sleeve 140 in position over a catheter 112. Monitoring bladders 130 are located on the sleeve 140 for monitoring pressure within a body cavity as described herein. In addition, the device depicted in FIG. 7 includes electromyography (EMG) electrodes 170 that can be used to assess muscle activity around a body cavity in addition to measuring pressure. The electrodes 170 may be located both proximally and distally of the array of monitoring bladders 130 as in the depicted embodiment. Alternatively, EMG electrodes may be provided on only the proximal side of the array of bladders 130 or only on the distal side of the array of bladders 130.

An electrical lead 174 is also depicted in FIG. 7 to connect the electrodes 170 to an electrical monitoring apparatus 176 that is configured to detect electrical activity in tissue contacting the electrodes 170. In some embodiments, the electrical monitoring apparatus 176 may be incorporated into the same housing as the pressure monitoring apparatus and in other embodiments, the different apparatus may be provided in separate housings.

The electrodes 170 may optionally be attached to expandable supports 172 such that they can be forced outwardly from the sleeve 140/catheter 112 to enhance their contact with surrounding tissue in a body cavity. The expandable supports 172 may take any suitable form, e.g., expandable balloons, structures constructed with shape memory materials, etc. The expandable supports 172 may preferably be expandable and collapsible between a collapsed configuration and an expanded configuration. In the collapsed configuration, the electrodes 170 are closer to the sleeve 140/catheter 112 and in the expanded configuration the electrodes are farther from the sleeve 140/catheter 112.

One embodiment of a method of using the body cavity pressure measurement systems described herein may include, for example, advancing the distal end of a pressure measurement device into and/or through a body cavity. Where rectal measurements are to be obtained, the device may be inserted in the rectum through the anus. The monitoring bladders and/or the distention device are preferably in their respective collapsed configurations to facilitate placement of the device. With the device in place (fluoroscopy, ultrasound, and other imaging/tracking systems ma be used to verify proper placement), the distention device may preferably be distended to fix the location of the device and, in the case of a rectal application, elicit the urge to defecate. The pressures in the rectum are monitored/measured using the one or more monitoring bladders on the device. If the bladders are mounted on a movable sleeve, the monitoring bladders may be retracted proximally in a stepwise manner and pressures are measured at selected locations. The selected locations may be determined using, for example, markers placed on the catheter, etc.

As used herein and in the appended claims, the singular forms "a," "and," and "the" include plural referents unless explicitly limited to the singular form or the context clearly dictates otherwise.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method of monitoring anal canal pressures comprising:
   locating a pressure measuring device in an anal canal and rectum, wherein the pressure measuring device comprises:
   a catheter comprising a proximal end and a distal end;
   a distention device mounted on the catheter proximate the distal end of the catheter, wherein the distention device is expandable and collapsible between a collapsed configuration and a distended configuration;
   a plurality of monitoring bladders mounted on the catheter at a location proximal to the distention device, wherein each monitoring bladder is movable along the catheter, and wherein the plurality of monitoring bladders are positioned about a periphery of the catheter at the same longitudinal position, wherein each monitoring bladder occupies only a portion of the periphery of the catheter and wherein the plurality of monitoring bladders are located in the anal canal; and
   a plurality of monitoring lumens, wherein each monitoring lumen of the plurality of monitoring lumens extends proximally through at least a portion of the catheter from the monitoring bladder towards the proximal end of the catheter, wherein each monitoring lumen is in fluid communication with an interior of one monitoring bladder such that a fluid pressure in the one monitoring bladder is communicated through the monitoring lumen;
   expanding the distention device to the distended configuration after locating the pressure measuring device in the anal canal and rectum; and
   monitoring pressure exerted by the anal canal at a first location using the plurality of monitoring bladders after expanding the distention device to the distended configuration, wherein pressure exerted by the anal canal on the plurality of monitoring bladders is measured independently of each other while the distention device is in the distended configuration.

2. A method according to claim 1, wherein the method further comprises:
   moving the plurality of monitoring bladders toward or away from the distention device after monitoring pressure exerted on the plurality of monitoring bladders by the anal canal at the first location using the plurality of monitoring bladders; and
   monitoring pressure exerted by the anal canal using the plurality of monitoring bladders after moving the plurality of monitoring bladders toward or away from the distention device while the distention device is in the distended configuration.

3. A method according to claim 2, the method further comprising holding the distention device in the distended configuration while moving the plurality of monitoring bladders toward or away from the distention device after monitoring pressure exerted on the plurality of monitoring bladders by the anal canal at the first location.

4. A method according to claim 1, wherein the distention device comprises a maximum transverse dimension in the distended configuration that is larger than any maximum transverse dimension of the pressure measuring device in the length occupied by the plurality of monitoring bladders, wherein the maximum transverse dimensions are measured transverse to the longitudinal axis.

5. A method according to claim 1, wherein the distention device is mounted at a fixed position on the catheter.

6. A method according to claim 1, wherein moving the plurality of monitoring bladders comprises moving a movable sleeve along the catheter, wherein the plurality of monitoring bladders are mounted on the movable sleeve.

7. A method according to claim 1, the method further comprising delivering fluid to the plurality of monitoring bladders before monitoring pressure exerted on the plurality of monitoring bladders by the anal canal.

* * * * *